United States Patent
Ciobanu et al.

(10) Patent No.: US 9,023,080 B2
(45) Date of Patent: May 5, 2015

(54) FLOW OBSTRUCTOR AND TRANSAPICAL CLOSURE DEVICE

(71) Applicant: Medtronic Vascular Galway Limited, Galway (IE)

(72) Inventors: Constantin Ciobanu, Galway (IE); Evin Donnelly, Galway (IE); Frank Harewood, Galway (IE); Padraig Savage, Santa Rosa, CA (US)

(73) Assignee: Medtronic Vascular Galway Limited, Ballybrit, Galway (IE)

( * ) Notice: Subject to any disclaimer, the term of this patent is extended or adjusted under 35 U.S.C. 154(b) by 185 days.

(21) Appl. No.: 13/658,025

(22) Filed: Oct. 23, 2012

(65) Prior Publication Data

US 2014/0114345 A1     Apr. 24, 2014

(51) Int. Cl.
*A61B 17/08*     (2006.01)
*A61B 17/00*     (2006.01)

(52) U.S. Cl.
CPC ... *A61B 17/0057* (2013.01); *A61B 2017/00606* (2013.01); *A61B 2017/00623* (2013.01); *A61B 2017/00632* (2013.01)

(58) Field of Classification Search
CPC .............. A61B 17/00623; A61B 2017/00579; A61B 2017/00601; A61B 2017/00575; A61B 2017/00606; A61B 17/3426; A61B 17/0293; A61B 2017/00265; A61B 2017/00592; A61B 2017/00632; A61B 2017/00637
USPC ............................ 623/1.1, 2.36; 606/213, 208
See application file for complete search history.

(56) References Cited

U.S. PATENT DOCUMENTS

| | | | |
|---|---|---|---|
| 2005/0246010 A1* | 11/2005 | Alexander et al. | 623/1.12 |
| 2010/0168778 A1 | 7/2010 | Braido | |
| 2012/0016411 A1* | 1/2012 | Tuval | 606/213 |

FOREIGN PATENT DOCUMENTS

WO    WO2010/139771     12/2010

* cited by examiner

*Primary Examiner* — Jonathan W Miles
*Assistant Examiner* — George J Ulsh

(57) ABSTRACT

Medical devices and methods for closing an anatomical aperture in a tissue are disclosed. The medical devices can include distal and proximal support structures, which can include a plurality of anchor members. A connection element can connect the distal and proximal support structures, and be configured to twist to create a seal within the medical device. In certain embodiments, a sheath about the medical device can be retracted to expose the distal support structure, which can allow it to revert to an anchoring configuration from a delivery configuration, such that the anchor members can engage an interior surface of the tissue. After twisting the connection element to form a seal, the sheath can be further retracted to expose the proximal support structure, which can allow it to revert to an anchoring configuration from a delivery configuration, such that the anchor members can engage an exterior surface of the tissue.

16 Claims, 3 Drawing Sheets

FLOW OBSTRUCTOR AND TRANSAPICAL CLOSURE DEVICE

BACKGROUND

1. Field

The present disclosure relates to medical devices and methods for closing anatomical apertures in a tissue. More specifically, the present disclosure relates to medical devices for closing entry points used during transapical procedures and to methods for closing anatomical apertures such as those created as entry points for accessing the heart during transapical, transaortic or other heart procedures. However, it is understood that the medical devices and methods disclosed herein can be used in other types of procedures and at other locations in the body for closing various anatomical apertures.

2. Background

There are numerous surgical procedures for accessing and operating on various parts of the heart. One method of accessing the interior of the heart uses a transapical approach. In transapical procedures, the apex of the heart can be accessed, such as by mini-sternotomy or thoracotomy. An incision can be made in the apex of the heart to provide an entry point for inserting, for example, a catheter to be used during the medical procedure.

Upon completion of the medical procedure, the entry point at the apex must be closed. One method of closing such an entry point is by sewing the entry point together with sutures. However, in a procedure performed on the beating heart, as can be the case in transapical procedures, there are certain risks associated with using sutures to pierce through the moving heart tissue. The medical devices and methods disclosed herein can provide fast and effective means for closing an entry point after performing a transapical procedure without the use of sutures.

BRIEF SUMMARY

The present disclosure relates to medical devices for closing anatomical apertures in a tissue, such as, but not limited to, entry points used during transapical heart procedures. It is understood that the medical devices and methods disclosed herein can also be used in other procedures such as, but not limited to, closing an opening in the septal wall.

Medical devices for closing an anatomical aperture in a tissue are disclosed herein. In certain embodiments the medical device can include a distal support structure, for example, a ring having a distal face and a proximal face. In certain embodiments, the distal face of the distal support structure can include a first plurality of anchor members. The medical device can also include a proximal support structure, for example, a ring having a distal face and a proximal face, where the proximal face can have a second plurality of anchor members. The medical device can also include a connection element connecting the distal support structure and the proximal support structure, where the connection element can be configured to be twisted to create a seal within the medical device.

In certain embodiments, a sheath restraining the medical device about a catheter can be retracted to expose the distal support structure, which can allow the distal support structure to revert to an anchoring configuration from a delivery configuration, such that the first plurality of anchor members can engage an interior surface of the tissue surrounding the anatomical aperture. After twisting the connection element to form a seal, the sheath can be further retracted to expose the proximal support structure, which can allow the proximal support structure to revert to an anchoring configuration from a delivery configuration, such that the second plurality of anchor members can engage an exterior surface of the tissue surrounding the anatomical aperture.

In certain embodiments, the distal and proximal support structures can be sinusoidal rings, where the anchor members are located at extradoses of the sinusoidal rings. In certain embodiments, the distal and proximal support structures can be made of a shape-memory alloy, biased to a curled position when in an anchoring configuration. In certain embodiments, the connection element can include a central support structure connecting the distal support structure and the proximal support structure. In certain embodiments, the central support structure can be made of a shape-memory alloy biased to a twisted position.

Delivery systems for delivering a medical device to close an anatomical aperture in a tissue are also disclosed. In addition to the medical device, the delivery system can also include a delivery catheter and a sheath. In certain embodiments, the sheath can restrain the medical device about the delivery catheter in a delivery configuration. In certain embodiments, an exterior of the delivery catheter can include retaining structures, configured to retain the medical device about the exterior of the delivery catheter. In certain embodiments, the delivery system can include an inner shaft within an interior lumen of the delivery catheter, such that the medical device can be restrained about the inner shaft by the sheath.

Methods of delivering a medical device and closing an anatomical aperture in a tissue are also disclosed. In certain embodiments, a delivery system such as the ones disclosed herein can be inserted through the anatomical aperture. A sheath can be retracted distally to expose the distal support structure of the medical device, which can allow the distal support structure to revert to an anchoring configuration from a delivery configuration, such that a first plurality of anchor members can engage an interior surface of the tissue surrounding the anatomical aperture. The delivery catheter can then be retracted distally to a position such that the distal end of the delivery catheter is proximal from the distal support structure and still engaged with the proximal support structure. The delivery system can then be rotated to twist the connection element connecting the distal and proximal support structures, forming a seal. The sheath can then be retracted further in the distal direction to expose the proximal support structure, which can allow the proximal support structure to revert to an anchoring configuration from a delivery configuration, such that a second plurality of anchor members can engage an exterior surface of the tissue surrounding the anatomical aperture.

In certain embodiments, where the connection element includes a central support structure connecting the distal and proximal support structures, rotating the delivery system can cause the central support structure to plastically deform, fixing the medical device in a twisted position. In certain embodiments, the central support structure can be made of a shape-memory alloy biased to a twisted position, such that when the sheath is retracted, the central support structure rotates into the twisted position.

In certain embodiments, the delivery system can include an inner shaft configured to deliver a primary medical device and a secondary medical device, which can be located proximally from the primary medical device and constrained about the inner shaft by a sheath. After delivering the primary medical device to an implantation location, the delivery catheter can be retracted in the distal direction to expose the inner shaft. The inner shaft can be positioned such that the secondary medical device is located with the distal support structure distal to an interior surface of the tissue surrounding the anatomical aperture and the proximal support structure is located proximal to the exterior surface of the tissue surrounding the anatomical aperture.

The sheath can be retracted distally to expose the distal support structure, which can allow the distal support structure to revert to an anchoring configuration from a delivery configuration, such that a first plurality of anchor members can engage an interior surface of the tissue surrounding the anatomical aperture. The inner shaft can then be retracted distally to a position such that the distal end of the inner shaft is proximal from distal support structure and still engaged with the proximal support structure. The delivery system can then be rotated to twist the connection element connecting the distal and proximal support structures, forming a seal within the medical device. The sheath can then be further retracted in the distal direction to expose the proximal support structure, which can allow the proximal support structure to revert to an anchoring configuration from a delivery configuration, such that a second plurality of anchor members can engage an exterior surface of the tissue surrounding the anatomical aperture. In certain embodiments, the inner shaft can include a plurality of retaining elements on an exterior surface of the inner shaft. The retaining elements can engage the proximal support structure of the secondary medical device to facilitate twisting the connection element when rotating the delivery system.

BRIEF DESCRIPTION OF THE DRAWINGS/FIGURES

DETAILED DESCRIPTION

While the disclosure refers to illustrative embodiments for particular applications, it should be understood that the disclosure is not limited thereto. Modifications can be made to the embodiments described herein without departing from the spirit and scope of the present disclosure. Those skilled in the art with access to this disclosure will recognize additional modifications, applications, and embodiments within the scope of this disclosure and additional fields in which the disclosed examples could be applied. Therefore, the following detailed description is not meant to be limiting. Further, it is understood that the systems and methods described below can be implemented in many different embodiments of hardware. Any actual hardware described is not meant to be limiting. The operation and behavior of the systems and methods presented are described with the understanding that modifications and variations of the embodiments are possible given the level of detail presented.

References to "one embodiment," "an embodiment," "in certain embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Figure 1B:
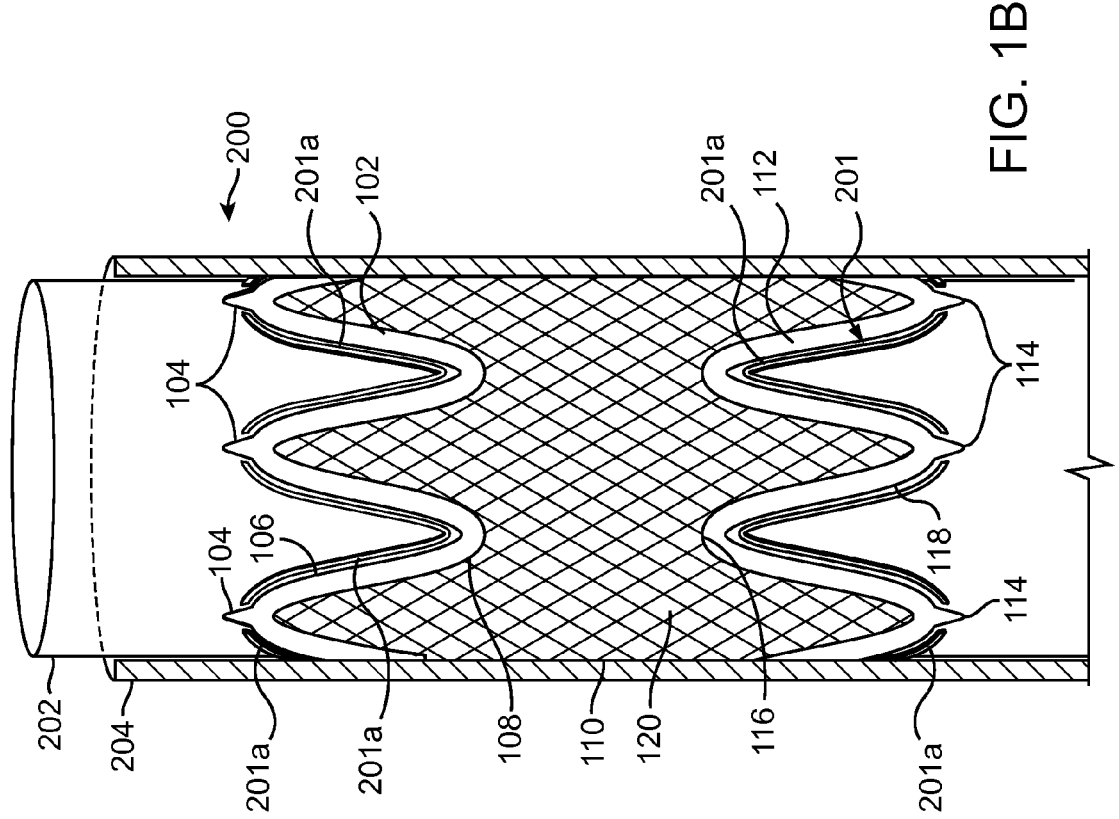
FIG. 1B illustrates the medical device loaded onto a catheter and covered by a sheath, according to an embodiment.
Figure 1A:
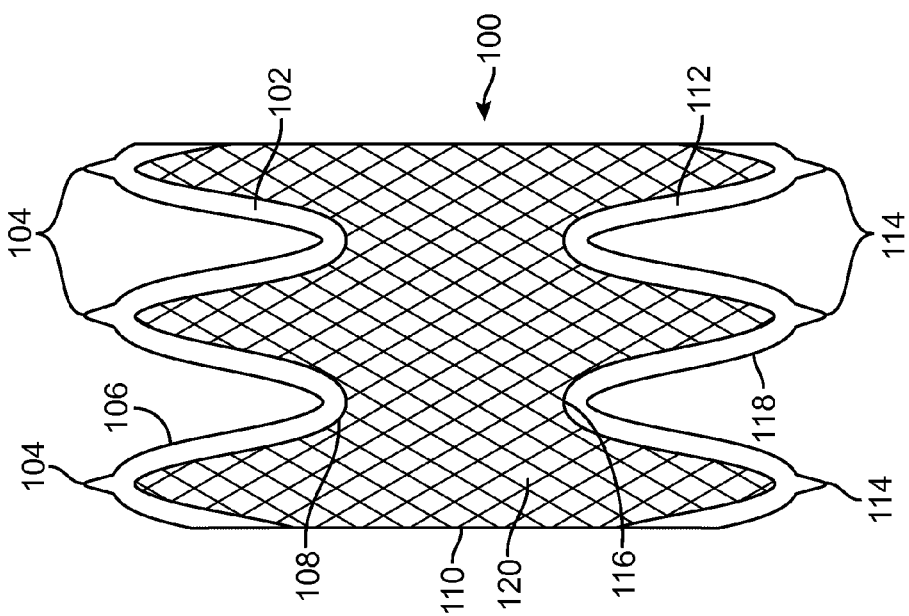
FIG. 1A illustrates the medical device in a delivery configuration, according to an embodiment.

FIG. 1A illustrates medical device 100 in a delivery configuration, which can be an uncurled or expanded state. Medical device 100 can include distal support structure 102, proximal support structure 112 and connection element 110, which can connect distal support structure 102 and proximal support structure 112. Distal support structure 102 can include distal face 106, proximal face 108, and anchor members 104. Similarly, proximal support structure 112 can include distal face 116, proximal face 118 and anchor members 114. In certain embodiments, distal and proximal support structures 102 and 112 can be sinusoidal rings, however, it is understood that distal and proximal support structures 102 and 112 can be any shape, uniform or non-uniform. For example, in certain embodiments, distal and proximal support structures 102 and 112 can be hexapedical, having six extradoses along a sinusoidal ring. In certain embodiments, anchor members 104 and 114 can be located at extradoses of the sinusoidal rings, as illustrated in FIG. 1A. Anchor members 104 and 114 can be, for example, hooks, barbs, spikes or any other element suitable for engaging tissue surrounding an anatomical aperture. In certain embodiments, all or portions of distal support structure 102, proximal support structure 112 and/or anchor members 104 and 114 can be a radiopaque material to facilitate locating medical device 100 using medical imaging during implantation.

In certain embodiments, distal and proximal support structures 102 and 112 can be made from a shape-memory alloy, such as, but not limited to, nitinol. In certain embodiments distal and proximal support structures 102 and 112 can be made from a suitable polymer with properties similar to that of a shape-memory alloy. In certain embodiments, distal and proximal support structures 102 and 112 can be biased to an anchoring configuration, for example, a curled position, when unconstrained by sheath 204. In certain embodiments, distal support structure 102 can be shape-set such that when unconstrained, distal face 106 can curl in the proximal direction, which can allow anchor members 104 to engage an interior surface of tissue surrounding an anatomical aperture. In certain embodiments, proximal support structure 112 can be shape-set such that when unconstrained, proximal face 118 can curl in the distal direction, which can allow anchor members 114 to engage an exterior surface of the tissue surrounding the anatomical aperture.

Connection element 110 can connect distal support structure 102 and proximal support structure 112. In certain embodiments, connection element 110 can be connected with sutures to distal and proximal support structures 102 and 112, although any suitable means of attaching connection element 110 can be used. Connection element 110 can be configured to be twisted, for example, about a central axis of medical device 100, in order to create a seal such that blood cannot pass through a central lumen of medical device 100. In certain embodiments, connection element 110 can be made from a blood-impermeable or impermeable material. In certain embodiments, connection element 110 can be an impermeable plastic material or nitinol foil, although any suitable material can be used for connection element 110. For example, connection element 110 can be made from materials such as, but not limited to, GORE-TEX®, DACRON® or polyester.

In certain embodiments, connection element 110 can include central support structure 120, which can connect distal and proximal support structures 102 and 112. Central support structure 120 can be located on an exterior or interior of connection element 110, or can be combined within connection element 110. For example, central support structure 120 can be connected to, or embedded within, connection element 110. Central support structure 120 can be made of any suitable material, such as, but not limited to, stainless steel or nitinol. In certain embodiments, such as when central support structure 120 is made of nitinol, central support structure 120 can be formed to a preset shape, biased to a twisted position. This can allow central support structure 120 to twist to the preset twisted position when unconstrained. In certain embodiments, central support structure 120 can be made from stainless steel, such as stainless steel wires. When twisted, the stainless steel can plastically deform, which can prevent central support structure 120 and connection element 110 from untwisting after being rotated by the delivery system. In certain embodiments, connection element 110 and/or central support structure 120 can be coated or impregnated with chemicals to promote tissue growth.

Figure 3A:
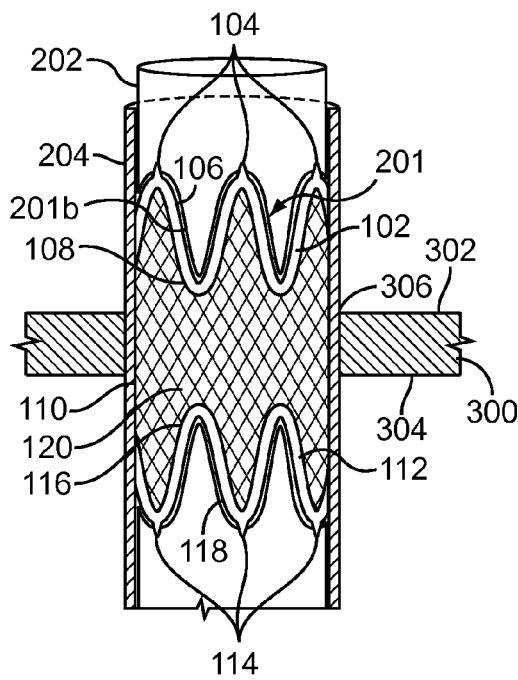
FIGS. 3A-3D illustrate the delivery and deployment sequence for the medical device, according to an embodiment.

FIG. 1B illustrates delivery system 200, with medical device 100 loaded about delivery catheter 202 and covered by sheath 204, according to an embodiment. Delivery catheter 202 can be the same catheter used to deliver a primary medical device, or it can be a separate catheter introduced after performing the primary procedure. Sheath 204 can be made from any suitable material capable of restraining medical device 100 about delivery catheter 202. For example, sheath 204 can be a rigid or flexible polymer material. In certain embodiments, delivery catheter 202 can include retaining elements 201, for example, ridges 201a, as shown in FIG. 1B, or grooves 201b, as shown in FIG. 3A, are configured to facilitate retaining medical device 100 about delivery catheter 202. For example, in certain embodiments, delivery catheter 202 can include grooves 201b, as shown in FIG. 3A, which correspond to the shape of distal and proximal support structures 102 and 112, such that distal and proximal support structures 102 and 112 fit within the grooves 201b.

Figure 2A:
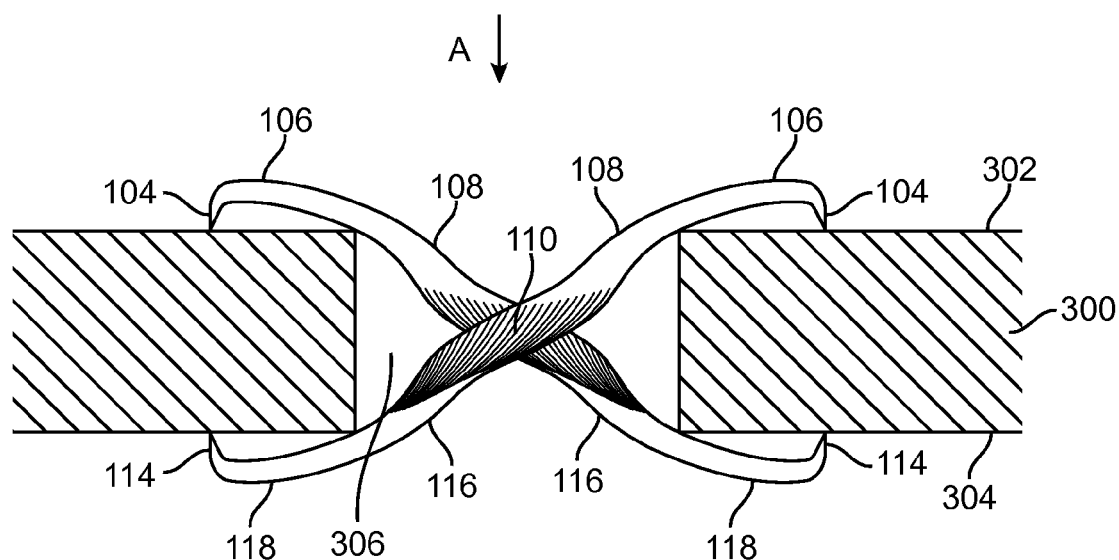
FIG. 2A illustrates the medical device after deployment, according to an embodiment.

FIG. 2A illustrates medical device 100 after being deployed, according to an embodiment. In certain embodiments, distal support structure 102 can curl in the proximal direction, and proximal support structure 112 can curl in the distal direction such that anchor members 104 and 114 can engage interior and exterior tissue surfaces 302 and 304 of tissue 300 surrounding the anatomical aperture. In certain embodiments, anchor members 104 and 114 can pierce tissue 300 to fix medical device 100 in place. In certain embodiments, deploying medical device 100 can pull tissue 300 together, decreasing the size of the anatomical aperture. As illustrated in FIG. 2A, connection element 110 can be twisted, forming a seal such that blood cannot pass from an interior to an exterior of tissue 300.

Figure 2B:
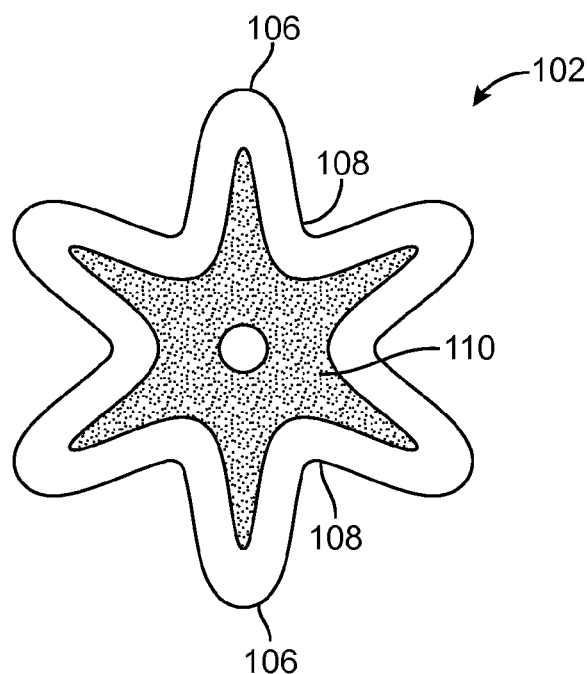
FIG. 2B illustrates a top view along direction A in FIG. 2A, according to an embodiment.

FIG. 2B illustrates a top view along direction A indicated in FIG. 2A, according to an embodiment. As shown, distal support structure 102 can curl to a preset configuration, which can be uniform or non-uniform. In the embodiment shown in FIG. 2A, the sinusoidal ring pattern of distal support structure 102 is splayed outward, which can allow anchor members 104 (not shown) to engage interior tissue surface 302 of tissue 300, as shown in FIG. 2A.

FIGS. 3A-3D illustrate the delivery and deployment sequence of medical device 100 using delivery system 200, according to an embodiment. FIG. 3A illustrates medical device 100 loaded onto delivery catheter 202 and covered by sheath 204. Delivery catheter 202 can be positioned within anatomical aperture 306 such that distal support structure 102 is located distally from interior tissue surface 302, and such that proximal support structure 112 is located proximally from exterior tissue surface 304. In certain embodiments, medical imaging techniques can be used to confirm the position of medical device 100.

Figure 3B:
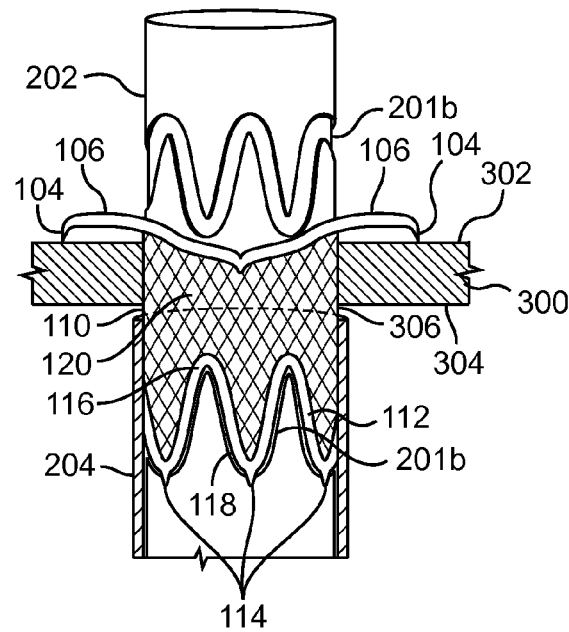

FIG. 3B illustrates retraction of sheath 204 in the distal direction, according to an embodiment. Distal support structure 102 can be uncovered, which can allow distal support structure 102 to revert to an anchoring configuration from a delivery configuration, for example, by curling in the proximal direction, such that anchor members 104 can engage interior tissue surface 302 of tissue 300 surrounding anatomical aperture 306. Proximal support structure 112 can remain covered by sheath 204 in a delivery configuration.

Figure 3C:
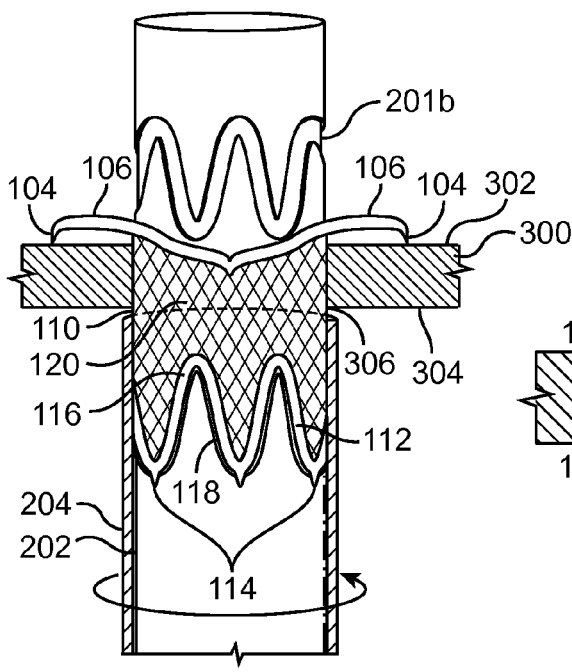

FIG. 3C illustrates twisting of connection element 110, according to an embodiment. Delivery catheter 202 can be retracted distally to a position such that a distal end of delivery catheter 202 is proximal from distal support structure 102. Delivery catheter 202 can still be engaged with proximal support structure 112. In certain embodiments, retaining elements on an exterior surface of delivery catheter 202 can facilitate twisting connection element 110, for example, by engaging proximal support structure 112. Delivery system 200 can then be rotated, as indicated by the arrow in FIG. 3C, to twist connection element 110, which can include central support structure 120, forming a seal. In certain embodiments, delivery system 200 can be rotated at least 360 degrees to form the seal.

Figure 3D:
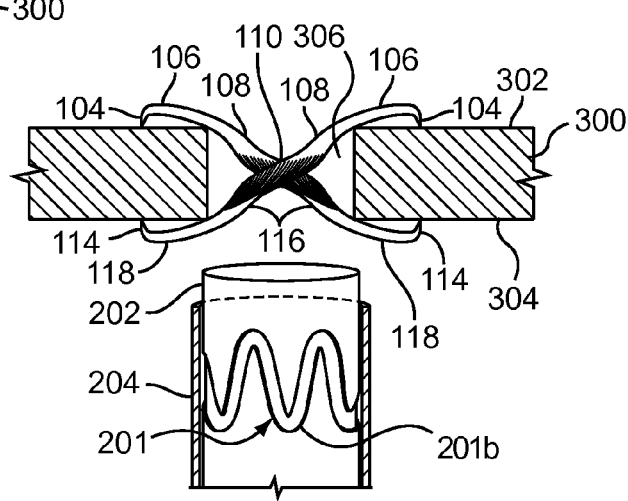

FIG. 3D illustrates medical device 100 after full retraction of sheath 204, according to an embodiment. Proximal support structure 112 can be uncovered, which can allow proximal support structure 112 to revert to an anchoring configuration from a delivery configuration, for example, by curling in the distal direction, such that the anchor members 114 can engage exterior tissue surface 304 of tissue 300 surrounding anatomical aperture 306. With medical device 100 in place, delivery catheter 202 and sheath 204 can be removed from the body.

Methods for delivering a medical device and closing an anatomical aperture in a tissue are also disclosed. In certain embodiments, a delivery system can be inserted through an anatomical aperture, such as an opening created in the apex of the heart to perform a transapical procedure. In certain embodiments, the delivery system can include a delivery catheter, a sheath, and a medical device restrained between the delivery catheter and the sheath, such as the medical devices disclosed herein. The sheath can be distally retracted to expose the distal support structure of medical device, which can allow the distal support structure to revert to an anchoring configuration from a delivery configuration, such that a first plurality of anchor members can engage an interior surface of the tissue surrounding the anatomical aperture. The delivery catheter can then be retracted distally to a position such that a distal end of the delivery catheter is proximal from the distal support structure, while still engaged with the proximal support structure. The delivery system can then be rotated to twist the connection element connecting the distal and proximal support structures, forming a seal within an interior of the medical device. The sheath can then be retracted further in the distal direction to expose a proximal support structure, which can allow the proximal support structure to revert to an anchoring configuration from a delivery configuration, such that a second plurality of anchor members can engage an exterior surface of the tissue surrounding the anatomical aperture.

In certain embodiments, where the connection element includes a central support structure connecting the distal and proximal support structures, rotating the delivery system can cause the central support structure to plastically deform, fixing the medical device in a twisted position. In certain embodiments, the central support structure can be made of a shape-memory alloy biased to a twisted position, such that when the sheath is retracted, the central support structure rotates into the twisted position.

The medical device can be preloaded about the delivery catheter and covered by the sheath, or it can be loaded onto the delivery catheter prior to the procedure. Loading the medical device about the delivery catheter can include manipulating the medical device from an anchoring configuration to a delivery configuration. In certain embodiments, this can include uncurling the medical device from a curled preset shape, positioning the medical device about the catheter, and covering the medical device with the sheath to secure the medical device about the catheter in an uncurled delivery configuration. In certain embodiments, the medical device can engage retaining structures, such as grooves or ridges on an exterior of the delivery catheter, to facilitate securing the medical device about the delivery catheter. In certain embodiments, the retaining elements on the exterior surface of the delivery catheter can facilitate twisting the connection element by engaging the medical device while twisting the delivery system.

In certain embodiments, the delivery system can include an inner shaft configured to deliver both a primary medical device and a secondary medical device. The primary medical device can be, for example, a prosthetic heart valve, and the secondary medical device can be, for example, a medical device such as those disclosed herein. In certain embodiments, the secondary medical device can be located proximally from the primary medical device, and constrained about the inner shaft by a sheath. The primary medical device can be delivered to an implantation location. The delivery catheter can then be retracted in the distal direction. The secondary medical device can then be positioned such that a distal support structure is located distally from the interior surface of the tissue and proximal support structure is located proximally from the exterior surface of the tissue. In certain embodiments, the tissue can be a heart wall. In certain embodiments, medical imaging can be used to facilitate positioning the secondary medical device properly within the anatomical aperture.

The sheath can be retracted distally to expose the distal support structure, which can allow the distal support structure to revert to an anchoring configuration from a delivery configuration, such that a first plurality of anchor members engage an interior surface of the tissue surrounding the anatomical aperture. The inner shaft can then be retracted distally to a position such that a distal end of the inner shaft is proximal from the distal support structure while still engaged with the proximal support structure. The delivery system, including the inner shaft, can then be rotated to twist the connection element connecting the distal and proximal support structures, forming a seal. The sheath can then be further retracted in the distal direction to expose the proximal support structure, which can allow the proximal support structure to revert to an anchoring configuration from a delivery configuration, such that a second plurality of anchor members can engage an exterior surface of the tissue surrounding the anatomical aperture.

The foregoing description has been presented for purposes of illustration and description. It is not intended to be exhaustive or to limit the precise embodiments disclosed. Other modifications and variations may be possible in light of the above teachings. The embodiments and examples were chosen and described in order to best explain the principles of the embodiments and their practical application, and to thereby enable others skilled in the art to best utilize the various embodiments with modifications as are suited to the particular use contemplated. By applying knowledge within the skill of the art, others can readily modify and/or adapt for various applications such specific embodiments, without undue experimentation, without departing from the general concept. Therefore, such adaptations and modifications are intended to be within the meaning and range of equivalents of the disclosed embodiments, based on the teaching and guidance presented herein.

What is claimed is:

1. A medical device for closing an anatomical aperture in a tissue having an interior surface and an exterior surface, comprising:
    a distal support structure comprising a ring having a distal face and a proximal face, the distal face having a first plurality of anchor members;
    a proximal support structure comprising a ring having a distal face and a proximal face, the proximal face having a second plurality of anchor members; and
    a connection element connecting the distal support structure and the proximal support structure, wherein the connection element is configured to be twisted about a central axis of the medical device to create a seal, such that the connection element in a twisted position closes a central lumen of the medical device that extends therethrough.

2. The medical device of claim 1, wherein the distal support structure is configured to revert to an anchoring configuration from a delivery configuration, such that the first plurality of anchor members engage the interior surface of the tissue, and wherein the proximal support structure is configured to revert to an anchoring configuration from a delivery configuration, such that the second plurality of anchor members engage the exterior surface of the tissue.

3. The medical device of claim 1, wherein the distal and proximal support structures each comprise a sinusoidal ring, wherein the anchor members are located at extradoses of the sinusoidal rings.

4. The medical device of claim 1, wherein the distal and proximal support structures are biased to an anchoring configuration.

5. The medical device of claim 4, wherein the distal and proximal support structures comprise a shape-memory alloy biased such that in the anchoring configuration, the distal face of the distal support structure is curled in the proximal direction, and the proximal face of the proximal support structure is curled in the distal direction.

6. The medical device of claim 1, wherein the anchor members are hooks.

7. The medical device of claim 1, wherein the connection element comprises a blood-impermeable material.

8. The medical device of claim 1, wherein the connection element further comprises a central support structure.

9. The medical device of claim 8, wherein the central support structure comprises a shape-memory alloy biased to the twisted position in which the central support structure twists about the central axis of the medical device.

10. The medical device of claim 1, wherein the connection element is rotatable 360 degrees from a delivery position to the twisted position.

11. A delivery system for delivering a medical device for closing an anatomical aperture in a tissue having an interior surface and an exterior surface, comprising:
- a delivery catheter;
- a sheath; and
- a medical device restrained between the delivery catheter and the sheath in a delivery configuration, the medical device comprising:
  - a distal support structure comprising a ring having a distal face and a proximal face, the distal face having a first plurality of anchor members;
  - a proximal support structure comprising a ring having a distal face and a proximal face, the proximal face having a second plurality of anchor members; and
  - a connection element connecting the distal support structure and the proximal support structure, wherein the connection element is configured to be twisted about a central axis of the medical device to create a seal, such that the connection element in a twisted position prevents blood flow through a central lumen of the medical device that extends therethrough.

12. The delivery system of claim 11, wherein exposing the distal support structure from the sheath allows the distal support structure to revert to an anchoring configuration such that the first plurality of anchor members engage the interior surface of the tissue, and wherein exposing the proximal support structure from the sheath allows the proximal support structure to revert to an anchoring configuration such that the second plurality of anchor members engage the exterior surface of the tissue.

13. The delivery system of claim 11, wherein the medical device is loaded about an exterior of the delivery catheter, and wherein the exterior of the delivery catheter comprises a plurality of retaining elements, configured to retain the medical device about the delivery catheter.

14. The delivery system of claim 11, further comprising an inner shaft within an interior lumen of the delivery catheter, wherein the medical device is restrained about the inner shaft by the sheath.

15. The delivery system of claim 11, wherein the connection element further comprises a central support structure, and wherein at least the distal and proximal support structures comprise a shape-memory alloy.

16. The delivery system of claim 11, wherein the connection element is rotatable 360 degrees from the delivery configuration to the twisted position.

\* \* \* \* \*